(12) United States Patent
Lenzenhuber (10) Patent No.: US 11,911,226 B2
(45) Date of Patent: Feb. 27, 2024

(54) ENERGY RECOVERY DEVICE

(71) Applicant: Aesculap AG, Tuttlingen (DE)

(72) Inventor: Frederick Lenzenhuber, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 365 days.

(21) Appl. No.: 17/312,561

(22) PCT Filed: Dec. 17, 2019

(86) PCT No.: PCT/EP2019/085746
§ 371 (c)(1),
(2) Date: Jun. 10, 2021

(87) PCT Pub. No.: WO2020/127340
PCT Pub. Date: Jun. 25, 2020

(65) Prior Publication Data
US 2022/0039911 A1    Feb. 10, 2022

(30) Foreign Application Priority Data

Dec. 19, 2018    (DE) ..................... 10 2018 132 962.8

(51) Int. Cl.
*A61B 90/70*    (2016.01)
*A61L 2/18*    (2006.01)
(Continued)

(52) U.S. Cl.
CPC ............... *A61B 90/70* (2016.02); *A61L 2/18* (2013.01); *A61L 2/26* (2013.01); *B08B 3/02* (2013.01);
(Continued)

(58) Field of Classification Search
None
See application file for complete search history.

(56) References Cited

U.S. PATENT DOCUMENTS

2010/0121141 A1    5/2010    Rontal
2011/0210268 A1    9/2011    Dornseifer
(Continued)

FOREIGN PATENT DOCUMENTS

CN    102164862 A    8/2011
CN    108362346 A    8/2018
(Continued)

OTHER PUBLICATIONS

International Search Report received in International Application No. PCT/EP2019/085746 dated Jul. 1, 2020, with translation, 10 pages.
(Continued)

*Primary Examiner* — Eric W Golightly
(74) *Attorney, Agent, or Firm* — Christopher A. Rothe; Culhane Meadows PLLC (57) ABSTRACT

An energy production device for a chargeable energy storage is arranged on a fluid conduit of an existing fluid circuit in a device through which a fluid flows. The fluid flow in the fluid conduit primarily serves a predetermined purpose different from that of the energy production device. The energy production device is arranged to produce energy from the kinetic energy of the fluid flow to charge the chargeable energy storage. A module insertable into the device may include the energy production device. The device may be a washer disinfector for processing medical instruments, systems and/or products that include at least one handpiece having a chargeable energy storage. The energy storage is configured as a rechargeable battery or as a power cell and is adapted to be processed together with the handpiece in the washer disinfector.

15 Claims, 4 Drawing Sheets

(51) Int. Cl.
    *A61L 2/26*     (2006.01)
    *B08B 3/02*     (2006.01)
    *B08B 9/032*     (2006.01)
    *B08B 13/00*     (2006.01)
    *F03B 13/00*     (2006.01)
    *H02J 50/10*     (2016.01)
    *H02J 7/00*     (2006.01)

(52) U.S. Cl.
    CPC ............ *B08B 9/0321* (2013.01); *B08B 13/00* (2013.01); *F03B 13/00* (2013.01); *A61L 2202/17* (2013.01); *A61L 2202/24* (2013.01); *B08B 2209/032* (2013.01); *F05B 2220/20* (2013.01); *F05B 2220/604* (2013.01); *H02J 7/0048* (2020.01); *H02J 50/10* (2016.02)

(56) References Cited

U.S. PATENT DOCUMENTS

2013/0294969 A1    11/2013    Chen et al.
2014/0265336 A1    9/2014    Aubuchon

FOREIGN PATENT DOCUMENTS

| | | |
|---|---|---|
| DE | 3320076 A1 | 12/1984 |
| EP | 2514386 A1 | 10/2012 |
| GB | 2516806 A | 2/2015 |
| JP | 200017707 A | 1/2000 |
| JP | 2007160201 A | 6/2007 |
| JP | 2014127720 A | 7/2014 |
| KR | 20130031171 A | 3/2013 |
| TW | 200925408 A | 6/2009 |
| TW | 201319388 A1 | 5/2013 |

OTHER PUBLICATIONS

Search Report received in German Application No. 10 2018 132 962.8 dated Oct. 29, 2019, with translation, 12 pages.
Written Opinion received in International Application No. PCT/EP2019/085746 dated Jul. 1, 2020, with translation, 22 pages.
Office Action received in Japanese Application No. 2021-535234 dated Aug. 7, 2023, with translation, 19 pages.
Office Action received in Chinese Application No. 201980077839.6 dated Dec. 1, 2023, with translation, 12 pages.

ENERGY RECOVERY DEVICE

CROSS-REFERENCE TO RELATED APPLICATION(S)

This application is the United States national phase entry of International Application No. PCT/EP2019/085746, filed Dec. 17, 2019, and claims the benefit of priority of German Application No. 10 2018 132 962.8, filed Dec. 19, 2018. The contents of International Application No. PCT/EP2019/085746 and German Application No. 10 2018 132 962.8 are incorporated by reference herein in their entireties.

FIELD

The invention relates to an energy production/energy conversion device for an energy storage, and in particular to an energy production/energy conversion device for an energy storage having a module for wireless and/or wired charging of the energy storage using a fluid flow present in a device.

BACKGROUND

Wireless systems, for example accumulator-powered systems with connectable energy storages, such as motor systems, surgical instruments in the field of medicine and the like, are increasingly entering the market, so that there is a general trend away from wired systems and towards wireless or so-called stand-alone systems with an energy storage ('battery'). These energy storages have to be supplied with electrical energy to ensure the operational readiness of the products they supply with energy.

The disadvantage here is that energy storage-based products and systems, such as motor-equipped handpieces in the field of medicine, first have to be charged before they can be used as intended.

A conventional solution is to decouple handpieces and energy storages and to keep charged exchangeable energy storages directly available at a treatment site, such as an operating room (OR). Sterilized handpieces are then equipped with the energy storages in the operating room. Further disadvantages are the additional handling required, the respective sizes of separate energy storages and the like.

Further miniaturization of corresponding systems and products is to be expected in the coming years, with smaller energy storage systems (rechargeable batteries, power cells and the like) being conceivable. At present, it is already foreseeable that these energy storages may be integrated into the handpiece or may be connectable as a smaller system.

In cases where such systems and/or handpieces have to be processed before they can be reused, as is often the case in the medical sector, for example, there is a need to process these systems and/or handpieces, i.e. also their energy storage or batteries, in a cleaning/disinfection device/washer disinfector (WD). One objective is therefore to move away from energy storages kept in the operating room and towards integrated energy storages. Separately required charging of the energy storage in the operating room then inevitably leads to unnecessary or unnecessarily complicated operating procedures and higher or even troubling expenditure, accompanied by correspondingly higher costs.

SUMMARY

The invention is therefore based on the object of providing an energy production/energy conversion device that enables systems with energy storages to be charged prior to use in the operating room, thereby improving manageability and usability of such systems.

In addition, the invention shall enable producing (generating, mining, recovering) or 'harvesting' and thus charging of energy storages in a WD.

According to a general idea underlying the invention, systems and/or products are to be charged by producing (generating), i.e. recovering (mining), 'harvesting', of electrical energy from an existing fluid circuit in order to enable charging of the systems before the use. At the same time, a data transmission interface is provided, via which a charging state can be read out, or a function is provided, which reports charging states of connected systems or products to the outside.

A concrete example of this general idea underlying the invention is, for example, in the medical field, to charge (surgical) systems and/or products used there, such as handpieces with integrated or connectable energy storages and the like in a product processing process by harvesting, i.e. obtaining or generating (electrical) energy in or from an existing fluid circuit, for example a water circuit, of a washer disinfector (WD), in order to enable the necessary charging of the systems and/or products before use in the operating room. An energy production/energy conversion device with corresponding performance can be designed as a module that can be read out via (by means of) a data transmission interface or reports the charging states of the connected products to the outside.

In other words—based on the above-mentioned, concrete example—the underlying general idea includes an energy production device or a module for wireless or wired charging of energy storages using the prevailing fluid pressure in a fluid flow or fluid circuit (for example, the water circuit in a washer disinfector) that is already provided or that already exists for other purposes. It is directly understood that neither the general idea nor the invention is limited to the medical field and there, in particular, to a fluid circuit of a WD and corresponding systems and/or products. What is decisive in the present invention is that electrical energy is recovered quasi as a waste product from already existing energy systems such as fluid flows for cooling/operating/cleaning etc., which can then be beneficially used for charging energy storages of surgical instruments.

Advantages according to the invention directly resulting from the possibility to charge systems and/or products by producing (generating, mining, harvesting) energy from a fluid circuit, for example during a processing process in a WD, include a significant saving of preparation time, a reduced handling effort at the site of use or application such as an OR, the immediate usability of systems and products at the site of use or application, and the possibility to recognize charging states via a data transmission interface, for example via an application for mobile devices, a software on a PC and the like.

In detail, the object is solved by an energy production/energy conversion device for a chargeable energy storage, wherein the energy production device is adapted to be arranged at/in a fluid line of an existing fluid circuit in a device (appliance), passed by a fluid flow, and (wherein) the fluid flow in the fluid line primarily serves a predetermined purpose (which is) different from that of the energy production. The energy production device is arranged to produce (generate, recover) electrical energy from the kinetic energy of the fluid flow for charging the chargeable energy storage.

Preferably, the energy production device has a modular design (module form) and is arranged to produce electrical energy by means of an energy harvesting process based on the fluid pressure in the existing fluid circuit of the device and to charge the energy storage with the energy thus produced.

Further preferably, the energy production device includes (has) a conversion unit for converting the fluid pressure of the fluid flow or the flow energy of the fluid into a rotational movement of, for example, a turbine, and a generator unit for converting the rotational movement into produced (generated) electrical energy.

Preferably, the conversion unit for converting the fluid pressure/flow energy into a rotational movement includes a rotor element having a predetermined geometry, which is rotatably mounted (supported) in a housing of the energy production device and in the fluid flow.

Preferably, the predetermined geometry is in a vane shape (impeller shape) or in a helical shape (screw shape). Alternatively, however, a so-called spherical turbine is also conceivable, consisting of a sphere along the equator line thereof circumferentially spaced pockets are recessed, which serve as pressure collecting troughs for the rotor-propelled drive of the sphere. The sphere itself can be penetrated centrally by a rotary shaft, which is rotatably mounted on both sides of the sphere.

Furthermore, preferably, in the energy production device, the conversion unit for converting the fluid pressure into a rotational movement can be an electric motor driven by the fluid flow during a flushing process, operating as a generator, which includes a rotor having a predetermined geometry, and which is configured to produce electric current in cooperation with a stator element, via (by means of) which the energy storage is chargeable via an induction device for inductively charging the energy storage or via a charging cable for wired charging of the energy storage.

Preferably, the energy production device includes (has) an electronic control arranged in a housing of the energy production device on a circuit board.

Preferably, the energy production device is configured to detect a filling level of the energy storage and to open a bypass upon detection of a predetermined (maximum) filling level, wherein the bypass is arranged to bypass the fluid flow past the conversion unit in the opened state, and wherein in this case the conversion unit is configured to stop both its rotation and the production (generation) of energy for charging the energy storage.

Preferably, the electrical energy produced by the generator unit can be transferred to the energy storage and/or a product by means of induction via a flexible circuit board having an induction line.

Alternatively, the energy produced by the generator unit is transferable in a wired manner to the energy storage via a charging cable.

Also preferably, the energy production device has the module, a device for determining a charging state of a connected energy storage and a data transmission interface via which the module can be read out or communicates the charging state to the outside.

A module including the energy production device is implementable, wherein the module is configured for use in a processing process (preparation process) for products, systems and/or instruments having an integrated or connectable, replaceable and chargeable energy storage, and to be held or stored in a processing device during the processing process. The module is characterized by an energy production device as described above; a connection for connecting the module to a fluid circuit of the processing device; a conduit for guiding a fluid through the module, (the fluid) flowing at the connection into the module; a port portion; at least one connection port for at least one product, system and/or instrument, (the at least one connection port being) provided at the port portion and configured to hold a product, system or instrument such that water flowing in via the connection port can flow through it; and an induction device, provided in a planar fashion under the connection port, where (in which) the energy storage (not shown) of the product, system and/or instrument connected to the connection port is located, (when) in the connected state, and (the induction device) configured to charge the energy storage via energy harvested from the fluid flow by the energy production device during operation of the processing device. Furthermore, an electronic control for controlling operations may be provided on the module.

In a practical case, the device is preferably a washer disinfector (WD, washing/disinfection device) for processing (preparing) medical instruments, systems and/or products, wherein the medical instruments, systems and/or products comprise at least one handpiece with a chargeable energy storage that can be connected (coupled) to and/or integrated in it, wherein the energy storage is configured as a rechargeable battery (accumulator) or as a power cell and is adapted to be processed together with the handpiece in the washer disinfector.

Then further preferred is a washer disinfector (WD, washing/disinfection device) for processing (preparing) medical instruments, systems and/or products, wherein the medical instruments, systems and/or at least one handpiece comprise a chargeable energy storage connectable thereto and/or integrated therein, wherein the energy storage is configured as a rechargeable battery or power cell and is adapted to be processed together with the handpiece in the washer disinfector. In the washer disinfector, an energy production device is configured a) to be held on a predetermined support or a predetermined sieve basket of the washer disinfector, or b) to be formed as a module integrated on a rinsing rack of the washer disinfector with an induction device for wireless transmission of energy via induction or (with) a charging cable arrangement for wired transmission of energy for charging a product connected to the washer disinfector, or c) to be formed as a module, (being) integrated on a predetermined support of the washer disinfector, (and) having an induction device for wireless transmission of energy via induction or (having) a charging cable arrangement for wired transmission of energy for charging of an instrument, which is accommodated in the washer disinfector and equipped with at least one energy storage, or of a product, which is connected to a tube portion of the washer disinfector.

In this case, the module may also be permanently installed in the washer disinfector (WD) and connected to at least one splash(-water)-permeable charging pad and/or at least one charging cable, wherein the charging pad is configured to inductively charge at least one product having at least one energy storage supported above the charging pad with the energy produced by the module, and the charging cable is configured to charge via the charging cable at least one individual product having an energy storage connected via the charging cable with the energy produced by the module.

BRIEF DESCRIPTION OF THE DRAWING FIGURES

The invention is described in more detail below with reference to the accompanying drawing figures. The following is shown.

In the figures, identical reference signs denote the same or at least equivalent parts and components. In this respect, a repeated, redundant description of such parts and components is omitted.

DETAILED DESCRIPTION

Preferred embodiments of an energy production device described herein are described below with reference to a washer disinfector (WD) known per se, such as is used in the medical field for processing reusable products, systems and/or instruments, as an example. For cleaning and disinfection, a WD uses a combination of mechanical, thermal and chemical treatments, which is similar to the principle of a dishwasher. Heated water, if applicable enriched with chemicals, is applied with pressure to the objects to be cleaned. It is understood that the invention is in no way limited to the medical field, to products, systems and/or instrumentation used there, or to the arrangement in or the use of a WD, but that correspondingly modified configurations and modifications are conceivable and implementable for numerous other and/or different products with integrated or connectable (exchangeable) energy storage and devices with a fluid circuit.

Figure 1:
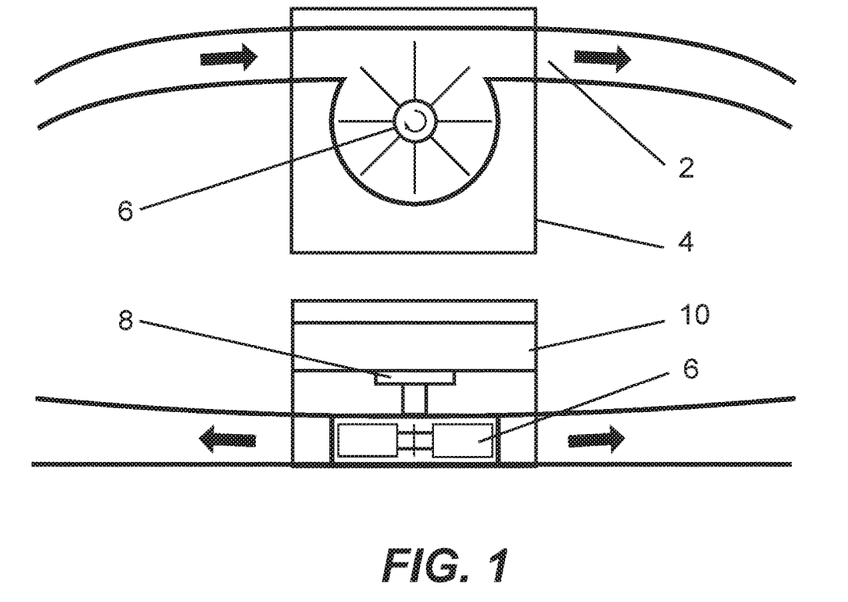
FIG. 1 shows a schematic representation of a principle of energy production using the energy or the pressure of a fluid flow in a tube portion of a device according to an embodiment.

FIG. 1 shows a schematic representation of a device in a front view and a top view for illustrating a principle of energy production using the energy or the pressure of a fluid flow in a tube portion of a device according to an embodiment example. In the present embodiment, the device is a washer disinfector (WD) known per se as described above.

In FIG. 1, a reference sign 2 indicates a tube portion or conduit portion of a fluid circuit in the device, for example a water circuit in the WD. A fluid flow/water flow with a predetermined fluid pressure/water pressure and/or a predetermined flow velocity in the tube portion 2 is indicated by black arrows.

A reference sign 4 denotes an energy production device according to the embodiment. The energy production device 4 has a conversion unit which is formed as a shaft or rotor 6 having a predetermined geometry, for example a vane-shaped geometry or a helical-shaped geometry, and which is arranged and configured to convert the longitudinal movement of the fluid flow in the tube portion 2 into a rotational movement. The fluid flow or the pressure thereof and/or the velocity thereof acts on the rotor 6 and causes it to rotate. For converting the rotational movement of the rotor 6 into energy, i.e. for generating energy, a generator device 8 is arranged and configured. The generator device 8 is connected to an electronic control 10, which may be arranged on a circuit board (not shown) and which is configured, inter alia, to control at least the energy production and the distribution of the produced (generated, harvested) energy as well as its predetermined conversion/output from the energy production device 4. The overall system as described above is housed in a fluid-tight manner in a housing.

In practice, the energy production uses the energy or the pressure of a fluid flow for so-called producing (mining, recovering) or 'harvesting' of energy, and the fluid flow or the water pressure thereof is used to drive a unit (the conversion unit or its rotor 6), which converts the water pressure in the tube portion 2 into a rotational movement, for example by means of a vane (an impeller), a helical shaft or the like. For the conversion of the rotational movement into energy, a generator (the generator device 8) is used. An electronic control 10 is located e.g. on the circuit board. The complete system is housed.

Figure 2:
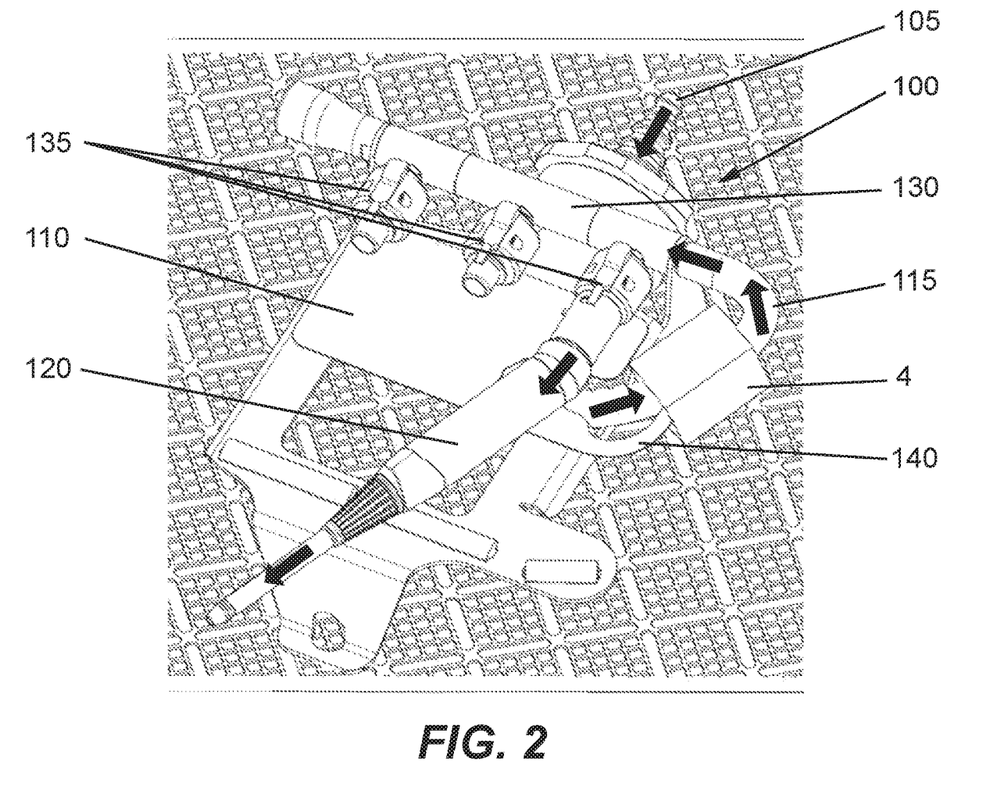
FIG. 2 shows a schematic representation of a module integrated on a rinsing rack in operative connection (cooperation) with an induction device for charging a respective energy storage of a plurality of products in an energy production device according to the embodiment.

FIG. 2 shows a schematic representation of a module 100 integrated on a rinsing rack of the WD in operative connection with an induction device 110 for charging an energy storage of a product, system or instrument 120 with an energy production device according to the embodiment. In this context, a rinsing rack is to be understood as a type of shelf comparable to a rinsing basket known per se in the WD, onto or into which parts to be processed can be placed or inserted. The rinsing rack is shown in FIG. 2 as a partial background structure.

The module 100 is configured to be placeable onto the rinsing rack, wherein brackets or fixation means may be provided. The module 100 includes a connection 105 for connecting the module 100 to the water circuit of the WD. Arrows in FIG. 2 indicate a flow path of water flowing through the module 100 during operation of the WD. As shown in FIG. 2, water enters the module 100 at the rear connection 105 and is guided to a port portion 130 via a conduit guide 115 (which in this embodiment includes the tube portion 2, but which may also be at least partially or entirely rigid). The port portion 130 has a plurality of connection ports 135 for products, systems and/or instruments. In this embodiment, for example, 3 connection ports 135 are provided, and according to FIG. 2, a handpiece 120 as one of a product, system or instrument is held at one of the connection ports 135 in such a way that it can be passed by water flowing in via the corresponding connection port 135.

Furthermore, the energy production device or energy production unit 4 shown in FIG. 1 is arranged in the conduit guide 115 in such a way that it can be passed by water flowing through the conduit guide 115 and develops the effect and function described above under FIG. 1. This means that during operation of the WD, water flows through the energy production device 4, the rotor 6 rotatably mounted therein rotates and, via (by mean of) the rotation, the generator device 8 connected to the rotor 6 harvests or produces (generates, mines, recovers) energy from the water flow primarily used for processing in the WD (and thus not primarily for energy production).

The produced energy is then converted by the electronic control 10 into a suitable form, for example, and put out to the induction device 110 via a conduit or induction line 140. The induction device 110 may include, for example, a flexible circuit board with an induction line as a suitable additional peripheral means. As shown in FIG. 2, the induction device 110 is arranged in a planar fashion under the connection ports 135 in an area where energy storages (not shown) of products, systems and/or instruments connected to the connection ports 135 come to lie in the connected state. In this way, these energy storages can be charged via the induction device 135 supplied by the energy production device with energy harvested from the water flow during the operation of the WD, i.e. during its processing operating procedure or cleaning and disinfection operating procedure.

The energy production device 4 for a chargeable energy storage is thus arranged at a fluid conduit of an existing fluid circuit in a device through which a fluid flows. The fluid flow in the fluid conduit primarily serves a predetermined purpose different from that of the energy production. The energy production device is arranged to produce energy from the fluid flow for charging the chargeable energy storage. The module 100 includes the energy production device 4 and an induction device 110 which is powered by energy produced (generated, mined, recovered, harvested) in the energy production device 4 and which is configured to charge energy storages provided in its induction field while the WD is performing its predetermined operating procedure and while the energy production device 4 is producing (harvesting) energy from the water circuit of the WD. In other words, 'harvested' energy is transferred to the products, systems and/or instruments via induction and thus suitable additional peripheral means, such as a flexible circuit board with an induction line. Alternatively, a charging connection via a +− pole connection and thus via a charging cable is also conceivable. The WD includes at least one module 100 configured to be held on at least one rinsing rack of the WD and to be connected to the water circuit of the WD.

In a modification of the embodiment described above, it can be provided that products, systems and/or instruments report back to the electronic control 10 that a predetermined filling level or state of charge of their energy storage has been reached. In this case, the electronic control 10 can be configured to mechanically cause an opening of a bypass device by means of suitable control, for example of an actuator or valve, which is arranged and configured to divert the water flow and to bypass the rotor 6, so that the rotor 6 does not rotate any further, as a result of which the generator device 8 does not produce any further energy, and thus charging of the energy storage is terminated or at least suspended for the opening duration of the bypass device.

Figure 3:
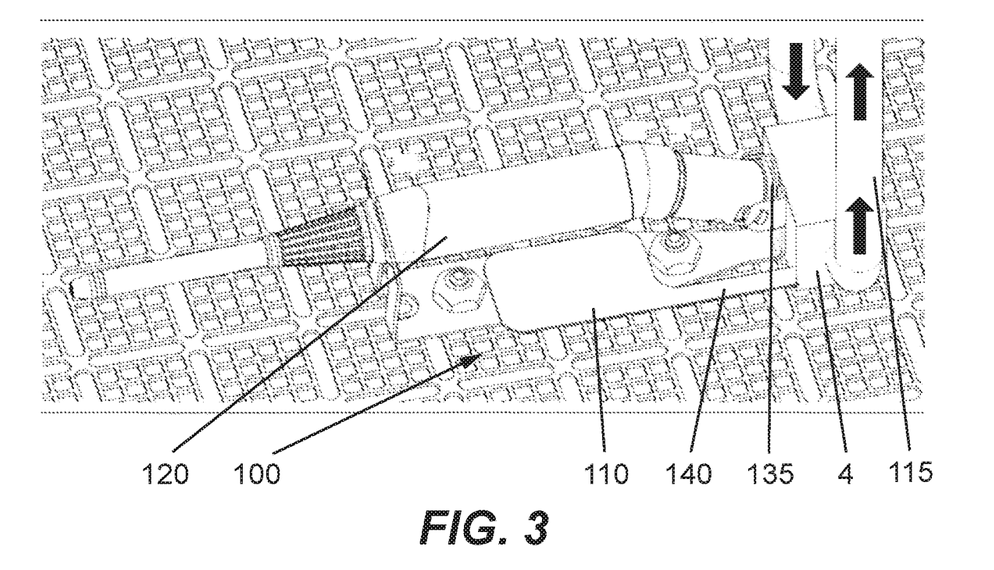
FIG. 3 shows a schematic representation of a module mounted in a sieve basket in operative connection with an induction device for charging an energy storage of a single product in an energy production device according to the embodiment.

FIG. 3 shows a schematic representation of a module 100 mounted in a sieve basket in operative connection with an induction device 135 for charging an energy storage of a product, system or instrument at an energy production device 4 according to the embodiment.

As shown in FIG. 3, in one modification, the module 100 of FIG. 2 may be configured to charge a (single) product, system or instrument. In this case, the configuration of the module may be simplified, for example, in that the (single) connection port 135 is installed directly on the energy production device 4. In addition, the induction device 110 can be correspondingly smaller. It is noted that FIG. 3 further shows screw connections of the module 100 to the rinsing rack or sieve basket for fixing it thereto or therein.

It is understood that the modification shown in FIG. 3 is not limited to charging a product, system, or instrument, and that any other products, systems, and/or instruments having an integrated or connectable, removable and chargeable energy storage are chargeable in a single configuration of the module 100.

For example, with an appropriate length, size and/or relocation of the conduit 140 or the induction device 110, for example a relocation or positioning to a position, in relative terms, further away from the energy production device 4, the energy storage of a space-consuming, i.e. larger, product, system or instrument, which occupies space and therefore requires a certain distance from other components, but as such does not need to be flushed and therefore does not require a connection to a connection port 135, can also be charged inductively. In such a case, the connection port 135 on the energy production device 4 can be omitted.

In a further modification of the preceding embodiment, which allows larger products, systems and/or instruments both in the preceding single configuration (having, as shown in FIG. 3, the connection port 135 directly at the energy production device 4) as well as in a module 100 with several connection ports 135, at least one connection for the conduit 140 to the induction device 110 can be formed to be pluggable and connection ports 135 can be closable mechanically and in a fluid-tight manner, for example by using an actuator and/or valve providing a closure device, which is driven by the electronic control 10, or by using a membrane or closure device or the like which opens/closes automatically upon connection/disconnection of a product, system or instrument.

In this case, a configuration may be such that when the electronic control 10 detects a presence of a product, system or instrument and/or of an induction device 110 connected to the energy production device 4, but detects that a corresponding connection port 135 is not occupied, i.e. when the electronic control detects that an energy storage of a product, system or instrument is to be charged, but that the product, system or instrument is not to be flushed and therefore has not been connected to the connection port 135, the electronic control 10 causes the connection port 135 to be closed in a fluid-tight manner and charging energy to be directed to the induction device 135 to charge the corresponding energy storage.

In the aforementioned configuration, space-consuming products, systems and/or instruments which, due to their size or construction, are not connectible to the at least one connection port 135 provided on the module 100 or the one connection port 135 provided on the energy production device 4, or which cannot be flushed and therefore are not connectible to the connection port 135 provided on the module 100 or the energy production device 4, may be processed with simultaneous charging of their energy storage even if the module 100 and/or the energy production device 4 has one or more connection ports 135. In other words, a space-consuming product, system or instrument does not require a specific embodiment (with/without connection port, respectively) of the module 100 and/or energy production device 4, but any products, systems or instruments may be processed and charged simultaneously using uniformly constructed modules 100 or energy production devices 4. It is noted that unoccupied connection ports 135 can be closed by default, so that a maximum fluid or water pressure affects at occupied ports.

Figure 4:
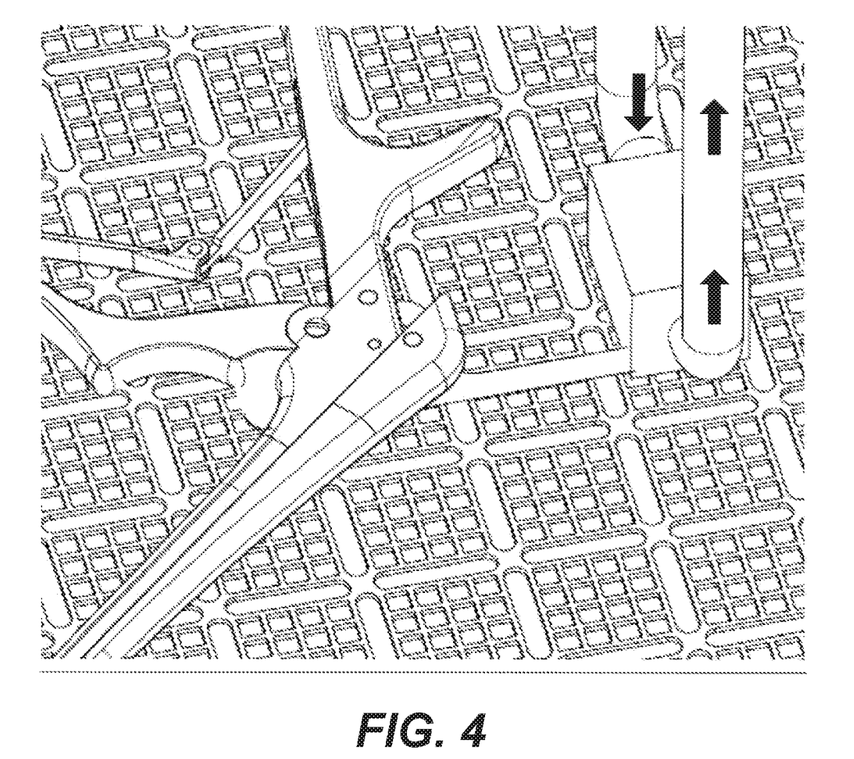
FIG. 4 shows relations, as described in connection with FIG. 3, in a schematic diagram.

FIG. 4 shows the relations, described above in connection with FIG. 3, in a schematic diagram. For reasons of simplicity and clarity, redundant reference signs are omitted in FIG. 4.

Figure 5:
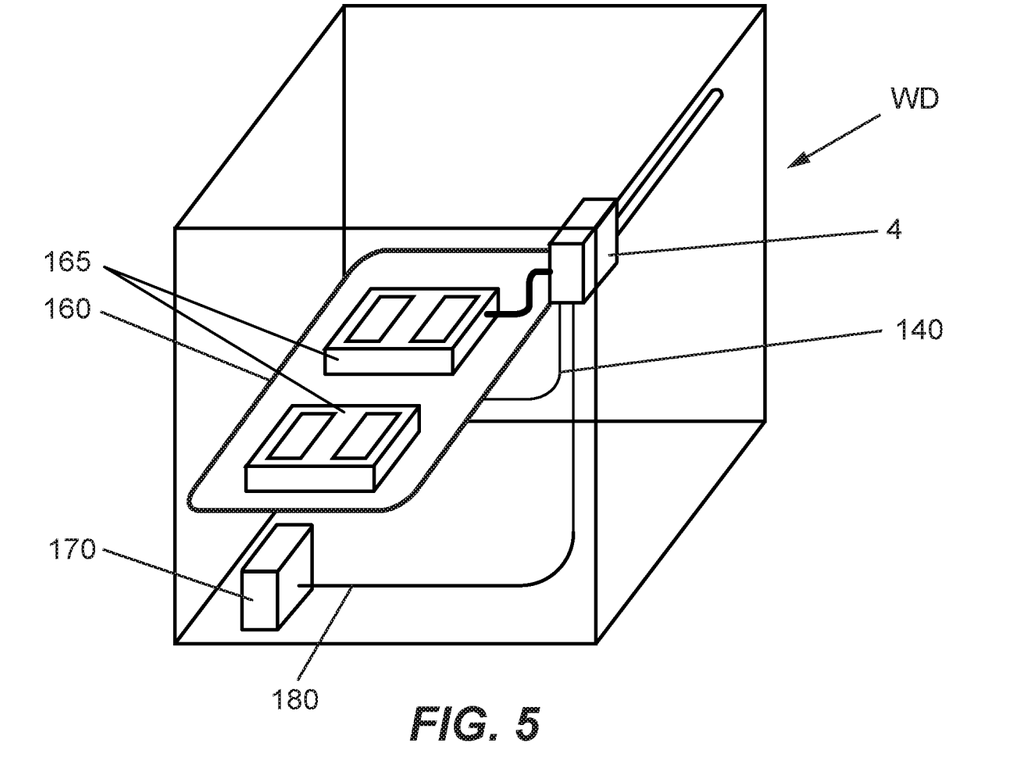
FIG. 5 shows a schematic representation of a module permanently installed in a washer disinfector with charging pads in an energy production device according to an embodiment.

FIG. 5 shows a schematic diagram of a module permanently installed in a washer disinfector with charging pads at an energy production device according to an embodiment (stand-alone variant).

According to the embodiment shown in FIG. 5, a module 100 (an energy production device 4) is permanently installed in a WD and connected to at least one charging pad 160, which can be configured to be permeable to splash (-water). Products, systems and/or instruments stored in sieve baskets 165 with integrated or connected, exchangeable energy storages can then be inductively charged with and without flushing above the at least one charging pad 160. Likewise, for example, individual products 170 with energy storage that are not adapted to be flushed may be connected directly to the energy production device 4 and charged via a (charging) cable 180.

Figure 6:
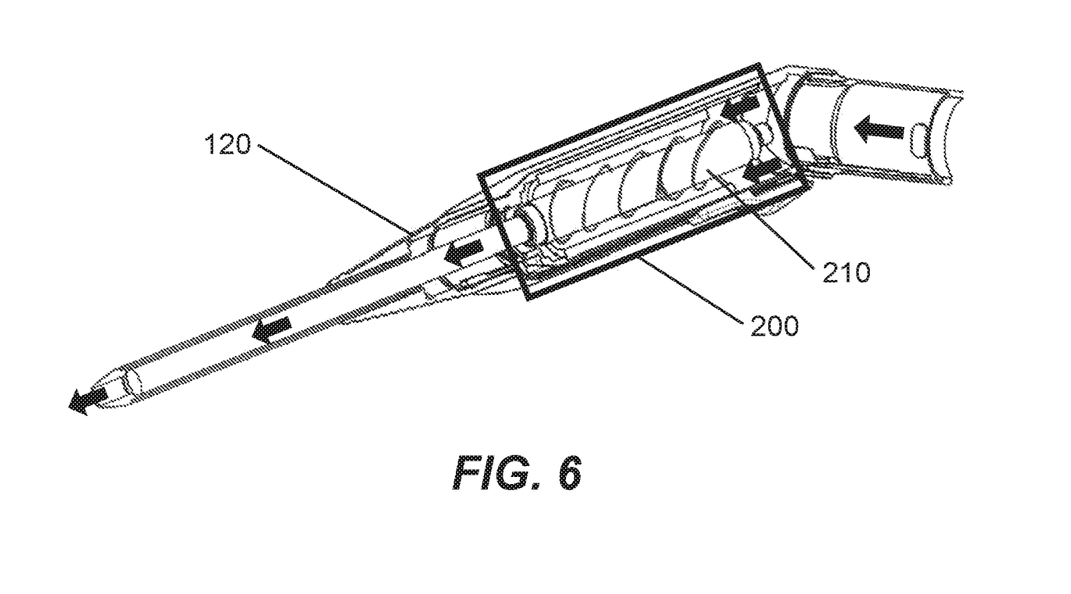
FIG. 6 shows a schematic representation of using an electric motor installed in a product as a generator for charging an energy storage of the product with energy produced in generator operation at an energy production device according to another embodiment.
Figure 7:
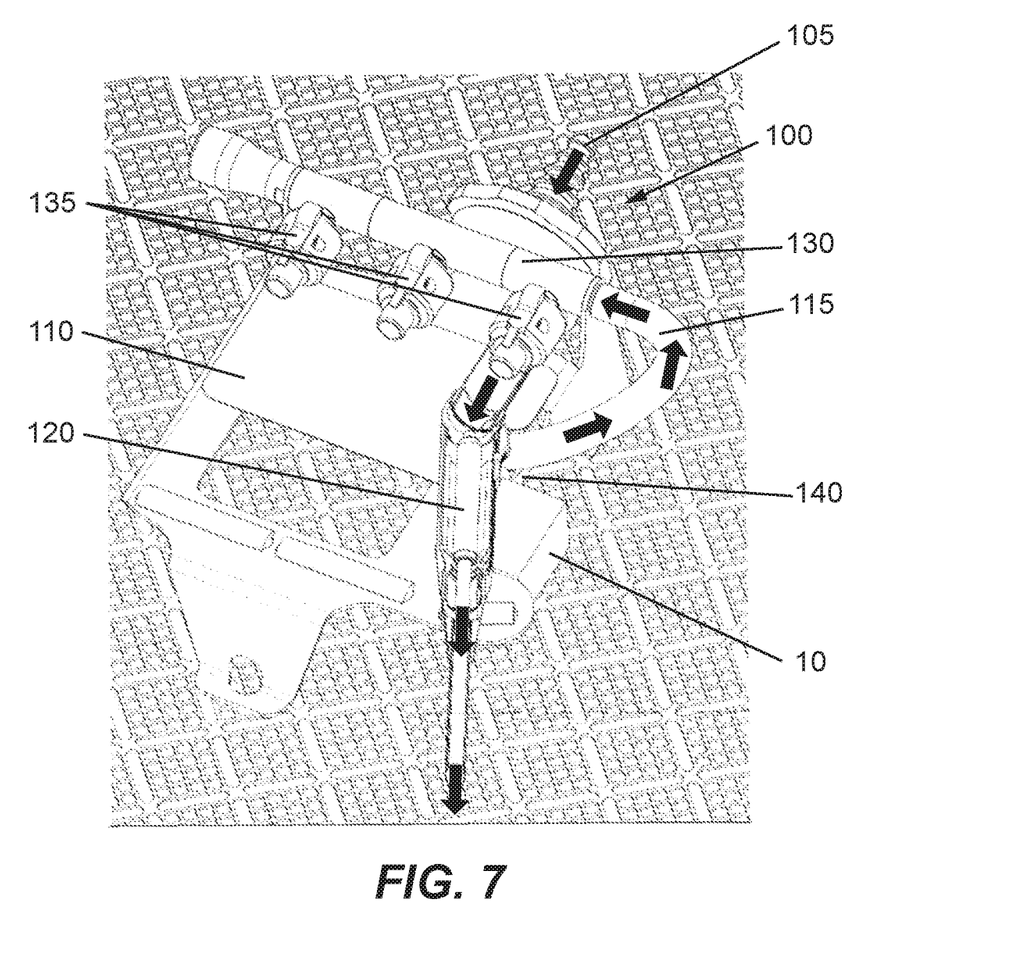
FIG. 7 shows a schematic representation of using the electric motor installed in a product as a generator for charging the energy storage of the product with energy produced in generator operation at an energy production device according to the other embodiment.

FIG. 6 shows, as a further modification, a schematic representation of using a flushed electric motor 200 installed in a product 120 as a generator for charging an energy storage (not shown) of the product with energy produced in generator mode at an energy production device or energy production module according to another embodiment. FIG. 7 shows a schematic representation of using the electric motor installed in a product as a generator for charging the energy storage of the product with energy produced in generator mode in an energy production device according to the other embodiment. According to FIG. 6 and FIG. 7, the energy production device 4 is, so to speak, relocated into the product, system or instrument, or the technical elements already present there are used for energy production in situ.

The electric motor 200 is used as a generator during flushing in the WD. A rotor 210 of the electric motor 200 which has a suitable geometry (e.g. helical-shaft shaped) produces an electric current in cooperation with a stator of the electric motor. The produced electric current is used to charge the energy storage via an induction device 110, alternatively via a charging cable (not shown). If necessary, an electronic control 10 is used. Otherwise, the module 100 shown in FIG. 7 corresponds to the module 100 shown in FIG. 2, with the exception of the energy production device 4 the function thereof, in this embodiment, is taken over by the electric motor 200 which is flushed and operated in generator mode during flushing.

As described above, an energy production device for a chargeable energy storage is arranged on a fluid conduit, through which a fluid flows, of an existing fluid circuit in a device. The fluid flow in the fluid conduit primarily serves a predetermined purpose different from that of the energy production device. The energy production device is arranged to produce energy from the kinetic energy of the fluid flow for charging the chargeable energy storage. A module insertable into the device may comprise the energy production device. In practice, the device may be a washer disinfector (WD) for processing medical instruments, systems and/or products, wherein the medical instruments, systems and/or products comprise at least one handpiece having a chargeable energy storage being connectable thereto and/or integrated therein, wherein the energy storage is configured as a rechargeable battery or as a power cell and is adapted to be processed together with the handpiece in the washer disinfector.

It is understood that the invention is not limited to the above-described embodiment, but that changes, modifications, combinations and equivalent arrangements within the scope of protection are also encompassed by the invention, wherein such changes, modifications, combinations and equivalent arrangements are readily obvious to the person skilled in the art.

The invention claimed is:

1. A module for use in a processing process for a medical product, system and/or instrument having an integrated or connectable, exchangeable and chargeable energy storage, the module being configured to be held or supported during the processing process in a washer disinfector as a processing device, the module comprising:
  a connection for connecting the module to an existing fluid circuit of the processing device;
  a conduit as a fluid conduit for guiding a fluid flow at the connection into and through the module;
  a port portion;
  at least one connection port provided at the port portion and configured to hold the medical product, system and/or instrument such that the medical product, system and/or instrument can be flushed by fluid flowing in through the connection port;
  an energy production device configured to be arranged on or in the fluid conduit, and arranged to produce energy from kinetic energy of the fluid flow for charging the energy storage; and
  an inductor arranged in an area in which the energy storage of the medical product, system and/or instrument is located in a connected state, and which is configured to charge the energy storage via energy harvested from the fluid flow via the energy production device, during operation of the washer disinfector.

2. The module according to claim 1 further comprising:
  a conversion unit for converting a fluid pressure of the fluid flow into a rotational movement; and
  a generator unit for converting the rotational movement into produced energy.

3. The module according to claim 2, wherein the conversion unit for converting the fluid pressure into the rotational movement comprises a rotor element with a predetermined geometry, which is rotatably mounted in a housing of the energy production device and which is lying in the fluid flow.

4. The module according to claim 3, wherein the predetermined geometry is formed in a vane shape or in a helical shape.

5. The module according to claim 2, wherein the conversion unit comprises an electric motor driven by the fluid flow during a flushing process and operable as the generator unit, the electric motor including the rotor and configured to produce electric current in cooperation with a stator element by which the energy storage is chargeable via the inductor for inductive charging of the energy storage.

6. The module according to claim 1, wherein the energy production device includes an electronic control arranged on a circuit board in a housing of the energy production device.

7. The module according to claim 6, wherein:
  the energy production device has a conversion unit for converting a fluid pressure of the fluid flow into a rotational movement and a generator unit for converting the rotational movement into produced energy; and
  the electronic control is configured to detect a filling level of the energy storage and to open a bypass upon detection of a predetermined filling level, wherein the bypass is arranged to guide the fluid flow in an opened state past the conversion unit, and wherein in the opened state the conversion unit is configured to stop rotation and stop production of energy for charging the energy storage.

8. The module according to claim 2, wherein the produced energy is transferable to the energy storage via an inductor that comprises a flexible circuit board with an induction line.

9. The module according to claim 1 further comprising a device for determining a charging state of the energy storage and a data transmission interface by which the module indicates the charging state.

10. The module according to claim 1, wherein the medical product, system and/or instrument comprises at least one handpiece with the energy storage which is connectable thereto and/or integrated therein, wherein the energy storage is configured as a rechargeable battery or as a power cell and is configured to be processed together with the handpiece in the washer disinfector.

11. A washer disinfector for processing a medical product, system and/or instrument, the washer disinfector comprising a module according to claim 1,
- the medical product, system and/or instrument comprising a handpiece with the energy storage connectable thereto and/or integrable therein,
- the energy storage configured as a rechargeable battery or power cell and configured to be processed in the washer disinfector together with the handpiece, and
- the energy production device of the module configured to be held at a predetermined support or a predetermined sieve basket of the washer disinfector.

12. A washer disinfector for processing a medical product, system and/or instrument, the washer disinfector comprising a module according to claim 1,
- the medical product, system and/or instrument comprising a handpiece with the energy storage connectable thereto and/or integrable therein,
- the energy storage configured as a rechargeable battery or power cell and configured to be processed in the washer disinfector together with the handpiece, and
- the module being integrated on a rinsing rack of the washer disinfector.

13. A washer disinfector for processing a medical product, system and/or instrument, the washer disinfector comprising a module according to claim 1,
- the medical product, system and/or instrument comprising a handpiece with the energy storage connectable thereto and/or integrable therein,
- the energy storage configured as a rechargeable battery or power cell and configured to be processed in the washer disinfector together with the handpiece, and
- the module integrated on a predetermined support of the washer disinfector or of a medical product, system and/or instrument connected to a tube portion of the washer disinfector, the induction device configured for wireless transmission of energy via induction for charging of a medical product, system and/or instrument, accommodated in the washer disinfector and equipped with at least one energy storage.

14. The washer disinfector according to claim 11, wherein the module is permanently installed in the washer disinfector and connected to at least one splash-water permeable charging pad, wherein the charging pad is configured to inductively charge the medical product, system and/or instrument, the medical product, system and/or instrument being supported on top of the charging pad.

15. A method of charging an energy storage of a surgical instrument comprising the following steps:
- connecting or inserting the surgical instrument to or into a washing and/or disinfection device;
- connecting a module according to claim 1 to the washer and/or disinfector device;
- connecting the energy storage to the energy production device of the module; and
- operating the washing and/or disinfection device.

* * * * *